(12) United States Patent
Tahri et al.

(10) Patent No.: US 7,465,727 B2
(45) Date of Patent: Dec. 16, 2008

(54) (1,10B-DIHYDRO-2-(AMINOALKYL-PHENYL)-5H-PYRAZOLO[1,5-C][1,3]BENZOXAZIN-5-YL)PHENYL METHANONE DERIVATIVES AS HIV VIRAL REPLICATION INHIBITORS

(75) Inventors: Abdellah Tahri, Anderlecht (BE); Lili Hu, Mechelen (BE); Dominique Louis Nestor Ghislain Surleraux, Braine-le-château (BE); Piet Tom Bert Paul Wigerinck, Terhagen (BE)

(73) Assignee: Tibotec Pharmaceuticals Ltd., Co Cork (IE)

( * ) Notice: Subject to any disclaimer, the term of this patent is extended or adjusted under 35 U.S.C. 154(b) by 0 days.

(21) Appl. No.: 11/909,747

(22) PCT Filed: Apr. 11, 2006

(86) PCT No.: PCT/EP2006/061499

§ 371 (c)(1),
(2), (4) Date: Sep. 26, 2007

(87) PCT Pub. No.: WO2006/108828

PCT Pub. Date: Oct. 19, 2006

(65) Prior Publication Data

US 2008/0214534 A1  Sep. 4, 2008

(30) Foreign Application Priority Data

Apr. 11, 2005 (EP) .................. 05102847

(51) Int. Cl.
C07D 498/04 (2006.01)
A61K 31/5365 (2006.01)
(52) U.S. Cl. ..................... 514/230.2; 544/95
(58) Field of Classification Search ............... 514/230.2; 544/95
See application file for complete search history.

(56) References Cited

FOREIGN PATENT DOCUMENTS

EP 0563733 A 10/1993
EP 1359147 A 11/2003

OTHER PUBLICATIONS

Orlov et al. Khimiya Geterotsiklicheskikh Soedinenii (1991), 8, 1131-1136 (Russian Journal, English translation).*
Orlov V D et al, "Substituted 1,10B-Dihydro-5H-Pyrazoloäl, 5-CÜ-1, 3-Benzo Xazines" Chemistry Of Heterocyclic Compounds (A Translation Of Khimiya Geterotsiklicheskikh Soedinenti), Aug. 1991, pp. 910-914, XP008055323 vol. 27, Plenum Press Co., New York, NY, US.

* cited by examiner

Primary Examiner—Kahsay T Habte
(74) Attorney, Agent, or Firm—Yunling Ren

(57) ABSTRACT

The present invention relates to 5H-pyrazolo[1,5-c][1,3]benzoxazin-5-yl)phenyl methanone derivatives as inhibitors of the viral replication of the HIV virus, processes for their preparation as well as pharmaceutical compositions, their use as medicines, and diagnostic kits comprising them. The present invention also concerns combinations of the present HIV inhibitors with other anti-retroviral agents. It further relates to their use in assays as reference compounds or as reagents. The compounds of the present invention are useful for preventing or treating infection by HIV and for treating AIDS.

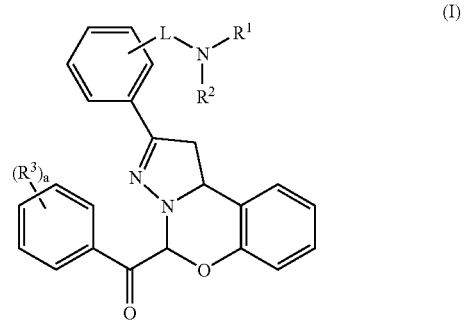

5 Claims, No Drawings

(1,10B-DIHYDRO-2-(AMINOALKYL-PHENYL)-5H-PYRAZOLO[1,5-C][1,3]BENZOXAZIN-5-YL) PHENYL METHANONE DERIVATIVES AS HIV VIRAL REPLICATION INHIBITORS

CROSS REFERENCE TO RELATED APPLICATIONS

This application claims priority of the benefits of the filing of Application Serial No. EP05102847.0 filed Apr. 11, 2005 and Application Serial No. PCT/EP2006/061499, filed Apr. 11, 2006. The complete disclosures of the aforementioned related patent applications are hereby incorporated herein by reference for all purposes.

The present invention relates to 5H-pyrazolo[1,5-c][1,3]benzoxazin-5-yl)phenyl methanone derivatives as inhibitors of the viral replication of the HIV virus, processes for their preparation as well as pharmaceutical compositions, their use as medicines, and diagnostic kits comprising them. The present invention also concerns combinations of the present HIV inhibitors with other anti-retroviral agents. It further relates to their use in assays as reference compounds or as reagents. The compounds of the present invention are useful for preventing or treating infection by HIV and for treating AIDS.

The number of people living with HIV/AIDS totaled in December 2004 about 40 million of which more than 37 million adults and about 2.2 million children under 15 years old. The people newly infected with HIV in 2004 alone rose to 4.9 million whereas there were in 2004 3.1 million AIDS deaths. Current chemotherapy for these people infected with HIV/AIDS employs the inhibitors of the viral fusion as well as reverse transcriptase (RT) and protease enzymes. In view of the emergence of HIV strains resistant to the current generation of fusion, RT and protease inhibitors, there exists an increasing need for the development of new and improved antivirals with different mechanisms of action.

EP 1359147 relates to benzoxazinones, in particular 1,4-dihydro-2H-3,1-benzoxazin-2-ones, or stereoisomeric forms or mixtures, or pharmaceutically acceptable salt forms thereof, which are useful as inhibitors of HIV reverse transcriptase, and to pharmaceutical compositions and diagnostic kits comprising the same, methods of using same for treating viral infection or as an assay standard or reagent, and intermediates and processes for making the same.

Orlov V. D. et al. (1991) disclose substituted 1,10b-dihydro-5H-pyrazolo[1,5-c]-1,3-benzoxazines, in particular 1,10b-dihydro-2-phenyl-5H-pyrazolo[1,5-c]-1,3-benzoxazin-5-yl) phenyl methanones having potential physiological activity.

EP0563733 relates to the use of known 7-oxo-7H-pyrido[1.2.3-de][1,4]benzoxazine-6-carboxylic acids and esters thereof as medicaments with antiviral activity.

The problem underlying the present invention is the provision of inhibitors of the viral replication of the HIV virus.

The present invention concerns the compounds having formula (I)

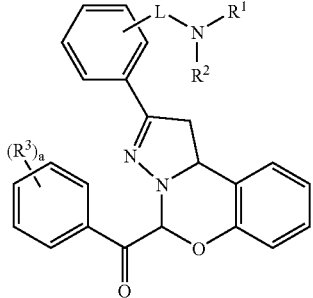

and the N-oxides, stereoisomeric forms and salts thereof, wherein a is zero, 1, 2, 3, 4 or 5;

L is $C_{1-4}$alkanediyl;

$R^1$ is hydrogen, $C_{1-10}$alkyl, $C_{2-10}$alkenyl, $C_{2-10}$alkynyl, $C_{3-12}$cycloalkyl, Het, aryl or $C_{1-10}$alkyl substituted with a substituent selected from the group consisting of Het, aryl, $C_{3-12}$cycloalkyl, amino and mono- or disubstituted amino wherein the substituents on the amino group are each individually selected from $C_{1-10}$alkyl, $C_{2-10}$alkenyl, $C_{3-12}$cycloalkyl, Het and aryl;

$R^2$ is hydrogen, $C_{1-10}$alkyl, $C_{2-10}$alkenyl, $C_{2-10}$alkynyl, $C_{3-12}$cycloalkyl, Het, aryl or $C_{1-10}$alkyl substituted with a substituent selected from the group consisting of Het, aryl, $C_{3-12}$cycloalkyl, amino and mono- or disubstituted amino wherein the substituents on the amino group are each individually selected from $C_{1-10}$alkyl, $C_{2-10}$alkenyl, $C_{3-12}$cycloalkyl, Het and aryl; or $R^1$ and $R^2$ taken together with the nitrogen atom to which they are attached form a 5 to 12 membered saturated or partially saturated heterocycle with one or more heteroatoms each individually selected from nitrogen, oxygen or sulfur, and wherein said heterocycle may optionally be substituted with $C_{1-10}$alkyl, $C_{2-10}$alkenyl, $C_{2-10}$alkynyl, $C_{3-12}$cycloalkyl, $C_{1-6}$alkyloxycarbonyl, Het, aryl or $C_{1-10}$alkyl substituted with a substituent selected from the group consisting of Het, aryl, $C_{3-12}$cycloalkyl, amino and mono- or disubstituted amino wherein the substituents on the amino group are each individually selected from $C_{1-10}$alkyl, $C_{2-10}$alkenyl, $C_{3-12}$cycloalkyl, Het and aryl;

$R^3$ is carboxyl, halogen, nitro, $C_{1-10}$alkyl, $C_{3-12}$cycloalkyl, polyhalo$C_{1-10}$alkyl, cyano, amino, mono- or disubstituted amino, aminocarbonyl, mono- or disubstituted aminocarbonyl, C $C_{1-10}$alkyloxy, $C_{1-10}$alkylthio, $C_{1-10}$alkylsulfonyl, pyrrolidinyl, piperidinyl, homopiperidinyl, morpholinyl, thiomorpholinyl or piperazinyl optionally substituted with $C_{1-10}$alkyl, wherein the substituents on any of the amino groups are each individually selected from $C_{1-10}$alkyl, $C_{2-10}$alkenyl, $C_{3-12}$cycloalkyl, Het and aryl;

aryl is phenyl optionally substituted with one or more substituents selected from the group consisting of C $C_{1-10}$alkyl, polyhalo$C_{1-10}$alkyl, C $C_{1-10}$alkyloxy, $C_{1-10}$alkylthio, $C_{1-10}$alkylsulfonyl, nitro, cyano, halo, $C_{3-7}$cycloalkyl, $C_{1-10}$alkylcarbonyl, carboxyl, $C_{1-10}$alkyloxycarbonyl, amino, mono- or disubstituted amino, amino-carbonyl, mono- or disubstituted aminocarbonyl, wherein the substituents on any of the amino groups are each individually selected from phenyl, $C_{1-10}$alkyl, $C_{2-10}$alkenyl, $C_{3-7}$cycloalkyl, pyrrolidinyl, piperidinyl, homopiperidinyl or piperazinyl optionally substituted with $C_{1-10}$alkyl;

Het is a 5 or 6 membered aromatic, saturated or partially saturated, monocyclic heterocycle with one or more heteroatoms each individually selected from nitrogen, oxygen or sulfur, and which heterocycle may optionally be substituted by one, or where possible, more than one substituent selected from the group consisting of $C_{1-10}$alkyl, polyhalo$C_{1-10}$alkyl, $C_{1-10}$alkyloxy, $C_{1-10}$alkylthio, $C_{1-10}$alkylsulfonyl, nitro, cyano, halo, $C_{3-7}$cycloalkyl, $C_{1-10}$alkylcarbonyl, carboxyl, $C_{1-10}$alkyloxycarbonyl, amino, mono- or disubstituted amino, aminocarbonyl, mono- or disubstituted aminocarbonyl, wherein the substituents on any of the amino groups are each individually selected from phenyl, $C_{1-10}$alkyl, $C_{2-10}$alkenyl, $C_{3-7}$cycloalkyl, pyrrolidinyl, piperidinyl, homopiperidinyl or piperazinyl optionally substituted with $C_{1-10}$alkyl.

As used herein, the term "halo" or "halogen" as a group or part of a group is generic for fluoro, chloro, bromo or iodo. The term "polyhalo" used as a prefix means substituted with one or more halogen atoms. Examples of the use of polyhalo as a prefix include for instance polyhalo$C_{1-10}$alkyl, polyhalo$C_{1-6}$alkyl, polyhalo$C_{1-4}$alkyl and the like. Particular interesting polyhaloalkyls are difluoromethyl and trifluoromethyl.

The term $C_{1-4}$alkyl as a group or part of a group means straight and branched chained saturated monovalent hydrocarbon radicals containing from 1 to 4 carbon atoms. Examples of such $C_{1-4}$alkyl radicals include methyl, ethyl, n-propyl, isopropyl, n-butyl, isobutyl, sec-butyl, tert-butyl and the like.

The term $C_{1-6}$alkyl as a group or part of a group means straight and branched chained saturated monovalent hydrocarbon radicals containing from 1 to 6 carbon atoms. Examples of such $C_{1-6}$alkyl radicals include methyl, ethyl, n-propyl, isopropyl, n-butyl, isobutyl, sec-butyl, tert-butyl, 2-methylbutyl, pentyl, iso-amyl, hexyl, 3-methylpentyl and the like.

The term $C_{1-10}$alkyl as a group or part of a group means straight and branched chained saturated monovalent hydrocarbon radicals containing from 1 to 10 carbon atoms. Examples of such $C_{1-10}$alkyl radicals include the examples of $C_{1-6}$alkyl radicals and heptyl, octyl, nonyl, decyl, 3-ethylheptyl and the like.

$C_{2-6}$alkenyl as a group or part of a group means straight and branched chained monovalent hydrocarbon radicals having at least one double bond and containing from 2 to 6 carbon atoms. Examples of such $C_{2-6}$alkenyl radicals include ethenyl, propenyl, 1-butenyl, 2-butenyl, isobutenyl, 2-methyl-1-butenyl, 1-pentenyl, 2-pentenyl, 1-hexenyl, 2-hexenyl, 3-hexenyl, 3-methyl-2-pentenyl and the like.

$C_{2-10}$alkenyl as a group or part of a group means straight and branched chained monovalent hydrocarbon radicals having at least one double bond and containing from 2 to 10 carbon atoms. Examples of such $C_{2-10}$alkenyl radicals include the examples of $C_{2-6}$alkenyl and 2-heptenyl, 3-heptenyl, 3-octenyl, 4-octenyl, 4-nonenyl, 4-decenyl and the like.

$C_{2-6}$alkynyl as a group or part of a group means straight and branched chained monovalent hydrocarbon radicals having at least one triple bond and containing from 2 to 6 carbon atoms. Examples of such $C_{2-6}$alkynyl radicals include ethynyl, propynyl, 1-butynyl, 2-butynyl, isobutynyl, 2-methyl-1-butynyl, 1-pentynyl, 2-pentynyl, 1-hexynyl, 2-hexynyl, 3-hexynyl, 3-methyl-2-pentynyl and the like.

$C_{2-10}$alkynyl as a group or part of a group means straight and branched chained monovalent hydrocarbon radicals having at least one triple bond and containing from 2 to 10 carbon atoms. Examples of such $C_{2-10}$alkynyl radicals include the examples of $C_{2-6}$alkynyl and 2-heptynyl, 3-heptynyl, 3-octynyl, 4-octynyl, 4-nonynyl, 4-decynyl and the like.

The term "$C_{1-2}$alkanediyl" as a group or part of a group defines bivalent straight and branched chained saturated hydrocarbon radicals having from 1 to 2 carbon atoms such as, for example, methylene, ethan-1,2-diyl, and the like.

The term "$C_{1-4}$alkanediyl" as a group or part of a group defines bivalent straight and branched chained saturated hydrocarbon radicals having from 1 to 4 carbon atoms such as the examples of $C_{1-2}$alkanediyl radicals, and propan-1,3-diyl, propan-1,2-diyl, butan-1,4-diyl, and the like.

The term $C_{3-7}$cycloalkyl as a group or part of a group means carbocyclic or spiro carbocyclic monovalent hydrocarbon radicals having from 3 to 7 carbon atoms in the backbone of the carbocycle or spirocarbocycle. Examples of such $C_{3-7}$cycloalkyl radicals include cyclopropyl, cyclobutyl, cyclopentyl, cyclohexyl, spiro[2.4]heptanyl, cycloheptyl and the like.

The term $C_{3-12}$cycloalkyl as a group or part of a group means carbocyclic or spiro carbocyclic monovalent hydrocarbon radicals having from 3 to 12 carbon atoms in the backbone of the carbocycle or spirocarbocycle. Examples of such $C_{3-12}$cycloalkyl radicals include the examples of $C_{3-7}$cycloalkyl and cyclooctyl, cyclononyl, spiro[4.4]nonyl, spiro[4.5]decyl, spiro[5.5]undecyl, cyclododecyl, spiro[5.6]dodecyl and the like.

Examples of 5 or 6 membered heterocycles as defined by Het include but are not limited to pyridine, pyrimidine, pyridazine, pyrazine, triazine, imidazole, thiazole, oxazole, oxadiazole, thiadiazole, isothiazole, isoxazole, pyrazole, furane, thiophene, pyrrole, quinoline, isoquinoline, benzoxazole, isobenzoxazole, benzothiazole, isobenzothiazole, benzimidazole, benzotriazole, tetrahydroquinoline, tetrahydroisoquinoline, piperidine, piperazine, morpholine, thiomorpholine, pyrrolidine, homopiperidine, homopiperazine, tetrahydrofurane and tetrahydrothienyl. As defined for Het, each of these exemplified heterocycles may optionally be further substituted.

As used herein, the term $C(=O)$ is meant to define a carbonyl moiety and the term $S(=O)_2$ is meant to define a sulfonyl moiety. As used herein, the term hydroxy means —OH, the term nitro means —$NO_2$, the term cyano means —CN, the term thio means —S, the term oxo means =O.

Whenever the terms "one or more substituents" or "substituted" are used in defining the compounds of formula (I), it is meant to indicate that one or more hydrogens on the atom indicated in the expressions using "one or more substituents" or "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

For therapeutic use, the salts of the compounds of the present invention are those wherein the counter-ion is pharmaceutically or physiologically acceptable. However, salts having a pharmaceutically unacceptable counter-ion may also find use, for example, in the preparation or purification of a pharmaceutically acceptable compound of the present invention. All salts, whether pharmaceutically acceptable or not are included within the ambit of the present invention.

The pharmaceutically acceptable or physiologically tolerable acid addition salt forms which the compounds of the present invention are able to form can conveniently be prepared using the appropriate acids, such as, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The compounds of the present invention containing an acidic proton may also be converted into their non-toxic metal or amine addition salt form by treatment with appropriate organic and inorganic bases. Appropriate base salt forms comprise, for example, the ammonium salts, quaternary ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms that the compounds of the present invention are able to form. Examples of such forms are e.g. hydrates, alcoholates and the like. The term "salts" also comprises the quaternization of the nitrogen atoms of the present compounds. A basic nitrogen can be quaternized with any agent known to those of ordinary skill in the art including, for instance, lower alkyl halides, dialkyl sulfates, long chain halides and arylalkyl halides.

The N-oxide forms of the present compounds are meant to comprise the compounds wherein one or several nitrogen atoms are oxidized to the so-called N-oxide.

The present compounds may also exist in their tautomeric forms. Such forms, although not explicitly indicated in the above formula, are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 80% of one isomer and maximum 20% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and 'diastereomerically pure' should be understood in a similar way, but then having regard to the enantiomeric excess and the diastereomeric excess respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of the compounds of the present invention can be separated into the individual diastereoisomers by conventional methods. Appropriate physical separation methods which may advantageously be employed are, for example, selective crystallization and chromatography, e.g. column chromatography.

The compounds may contain one or more asymmetric centers and thus may exist as different stereoisomeric forms. The absolute configuration of each asymmetric center that may be present in the compounds may be indicated by the stereochemical descriptors R and S, this R and S notation corresponding to the rules described in Pure Appl. Chem. 1976, 45, 11-30.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

Whenever used in the present patent application, the terms "present compounds", "compounds of the present invention", "compounds of formula (I)" or similar terms are meant to comprise the compounds of formula (I), their N-oxides, their stereoisomeric forms, their salt forms or any subgroup thereof.

Interesting compounds are those compounds of formula (I) or any subgroup thereof wherein a is zero, 1 or 2; more in particular wherein a is zero or 1.

Other interesting compounds are those compounds of formula (I) or any subgroup thereof wherein $R^1$ is hydrogen, $C_{1-6}$alkyl, $C_{2-6}$alkenyl, $C_{2-6}$alkynyl, $C_{3-7}$cycloalkyl, Het, aryl or $C_{1-6}$alkyl substituted with a substituent selected from the group consisting of Het, aryl, $C_{3-7}$cycloalkyl, amino and mono- or disubstituted amino wherein the substituents on the amino group are each individually selected from $C_{1-6}$alkyl or $C_{3-7}$cycloalkyl; in particular wherein $R^1$ is $C_{1-6}$alkyl, $C_{3-7}$cycloalkyl, Het, aryl or $C_{1-6}$alkyl substituted with a substituent selected from the group consisting of Het, aryl, $C_{3-7}$cycloalkyl and mono- or disubstituted amino wherein the substituents on the amino group are each individually selected from $C_{1-6}$alkyl.

Other interesting compounds are those compounds of formula (I) or any subgroup thereof wherein $R^2$ is hydrogen, $C_{1-10}$alkyl, $C_{2-10}$alkenyl, $C_{2-10}$alkynyl, $C_{3-12}$cycloalkyl, or $C_{1-10}$alkyl substituted with a substituent selected from the group consisting of Het, aryl, $C_{3-7}$cycloalkyl, amino and mono- or disubstituted amino wherein the substituents on the amino group are each individually selected from $C_{1-6}$alkyl; in particular wherein $R^2$ is hydrogen, $C_{1-6}$alkyl, $C_{2-6}$alkenyl, or $C_{1-6}$alkyl substituted with a substituent selected from the group consisting of aryl.

Other interesting compounds are those compounds of formula (I) or any subgroup thereof wherein $R^1$ and $R^2$ taken together with the nitrogen atom to which they are attached form a 5 to 12 membered saturated or partially saturated heterocycle which heterocycle may optionally be substituted with $C_{1-6}$alkyl, $C_{2-6}$alkenyl, $C_{2-6}$alkynyl, $C_{3-7}$cycloalkyl, $C_{1-6}$alkyloxycarbonyl, Het, aryl or $C_{1-6}$alkyl substituted with a substituent selected from the group consisting of Het, aryl, $C_{3-7}$cycloalkyl, amino and mono- or disubstituted amino wherein the substituents on the amino group are each individually selected from $C_{1-6}$alkyl, $C_{2-6}$alkenyl, $C_{3-7}$cycloalkyl, Het and aryl; in particular wherein $R^1$ and $R^2$ taken together with the nitrogen atom to which they are attached form a 5 to 12 membered saturated or partially saturated heterocycle which heterocycle may optionally be substituted with $C_{1-6}$alkyl, $C_{1-6}$alkyloxycarbonyl or $C_{1-6}$alkyl substituted with aryl; more in particular wherein $R^1$ and $R^2$ taken together with the nitrogen atom to which they are attached form a heterocycle selected from the group consisting of piperazinyl, homopiperazinyl, piperidinyl, homopiperidinyl, morpholinyl, thiomorpholinyl, pyrrolidinyl, indolinyl, 1,2,3,4-tetrahydroquinolinyl, 1,2,3,4-tetrahydro-isoquinolinyl, which heterocycle may optionally be substituted with $C_{1-6}$alkyl, $C_{2-6}$alkenyl, $C_{2-6}$alkynyl, $C_{3-7}$cycloalkyl, $C_{1-6}$alkyloxycarbonyl, Het, aryl or $C_{1-6}$alkyl substituted with a substituent selected from the group consisting of Het, aryl, $C_{3-7}$cycloalkyl, amino and mono- or disubstituted amino wherein the substituents on the amino group are each individually selected from $C_{1-6}$alkyl, $C_{2-6}$alkenyl, $C_{3-7}$cycloalkyl, Het and aryl; and even more in particular wherein $R^1$ and $R^2$ taken together with the nitrogen atom to which they are attached form a heterocycle selected from the group consisting of piperazinyl, homopiperazinyl, piperidinyl, homopiperidinyl, morpholinyl, thiomorpholinyl, pyrrolidinyl, indolinyl, 1,2,3,4-tetrahydroquinolinyl, 1,2,3,4-tetrahydroisoquinolinyl, which heterocycle may optionally be substituted with $C_{1-6}$alkyl, $C_{1-6}$alkyloxycarbonyl or $C_{1-6}$alkyl substituted with aryl.

Other interesting compounds are those compounds of formula (I) or any subgroup thereof wherein $R^3$ is carboxyl, halogen, nitro, $C_{1-6}$alkyl, $C_{3-7}$cycloalkyl, polyhalo-$C_{1-4}$alkyl, cyano, amino, mono- or disubstituted amino, aminocarbonyl, mono- or disubstituted aminocarbonyl, $C_{1-6}$alkyloxy, $C_{1-6}$alkylthio, $C_{1-6}$alkylsulfonyl, pyrrolidinyl, piperidinyl, homopiperidinyl, morpholinyl, thiomorpholinyl or piperazinyl optionally substituted with $C_{1-6}$alkyl, wherein the substituents on any of the amino groups are each individually selected from $C_{1-6}$alkyl, $C_{2-6}$alkenyl, $C_{3-7}$cycloalkyl, Het and aryl; in particular wherein $R^3$ is halogen, nitro, $C_{1-6}$alkyl, $C_{3-7}$cycloalkyl, polyhalo$C_{1-4}$alkyl, cyano, $C_{1-6}$alkyloxy, $C_{1-6}$alkylthio, $C_{1-6}$alkylsulfonyl, piperidinyl, morpholinyl.

Other interesting compounds are those compounds of formula (I) or any subgroup thereof wherein aryl is phenyl optionally substituted with one or more substituents selected from the group consisting of $C_{1-6}$alkyl, polyhalo$C_{1-6}$alkyl, $C_{1-6}$alkyloxy, $C_{1-6}$alkylthio, $C_{1-6}$alkylsulfonyl, nitro, cyano, halo, $C_{3-7}$cycloalkyl, $C_{1-6}$alkylcarbonyl, carboxyl, $C_{1-6}$alkyloxycarbonyl, amino, mono- or disubstituted amino, aminocarbonyl, mono- or disubstituted aminocarbonyl, wherein the substituents on any of the amino groups are each individually selected from phenyl, $C_{1-6}$alkyl, $C_{2-6}$alkenyl, $C_{3-7}$cycloalkyl, pyrrolidinyl, piperidinyl, homopiperidinyl or piperazinyl optionally substituted with $C_{1-6}$alkyl; in particular wherein aryl is phenyl optionally substituted with one, two or three substituents selected from the group consisting of $C_{1-6}$alkyl, $C_{1-6}$alkyloxy, nitro, cyano, halo, amino, mono- or disubstituted amino, wherein the substituents on any of the amino groups are each individually selected from $C_{1-6}$alkyl.

Other interesting compounds are those compounds of formula (I) or any subgroup thereof wherein Het is a 5 or 6 membered aromatic, saturated or partially saturated, monocyclic or bicyclic heterocycle with one or more heteroatoms each individually selected from nitrogen, oxygen or sulfur, and which heterocycle may optionally be substituted by one, or where possible, more than one substituent selected from the group consisting of $C_{1-6}$alkyl, polyhalo$C_{1-6}$alkyl, $C_{1-6}$alkyloxy, $C_{1-6}$alkylthio, $C_{1-6}$alkylsulfonyl, nitro, cyano, halo, $C_{3-7}$cycloalkyl, $C_{1-6}$alkylcarbonyl, carboxyl, $C_{1-6}$alkyloxycarbonyl, amino, mono- or disubstituted amino, aminocarbonyl, mono- or disubstituted aminocarbonyl, wherein the substituents on any of the amino groups are each individually selected from phenyl, $C_{1-6}$alkyl, $C_{2-6}$alkenyl, $C_{3-7}$cycloalkyl, pyrrolidinyl, piperidinyl, homopiperidinyl or piperazinyl optionally substituted with $C_{1-6}$alkyl; in particular wherein Het is a 5 or 6 membered aromatic, saturated or partially saturated, monocyclic or bicyclic heterocycle with one or more heteroatoms each individually selected from nitrogen, oxygen or sulfur, and which heterocycle may optionally be substituted with $C_{1-6}$alkyl; more in particular wherein Het is a heterocycle selected from the group consisting of pyridinyl, pyrimidinyl, pyrazinyl, pyridazinyl, triazinyl, pyranyl, pyrrolyl, furanyl, thienyl, oxazolyl, isoxazolyl, thiazolyl, isothiazolyl, imidazolyl, tetrahydrofuranyl, tetrahydrothienyl, imidazolinyl, dioxolanyl, pyrrolidinyl, piperidinyl, homopiperidinyl, piperazinyl, homopiperazinyl, dioxanyl, morpholinyl, thiomorpholinyl, which heterocycle may optionally be substituted by one, or where possible, more than one substituent selected from the group consisting of $C_{1-6}$alkyl, polyhalo$C_{1-6}$alkyl, $C_{1-6}$alkyloxy, $C_{1-6}$alkylthio, $C_{1-6}$alkylsulfonyl, nitro, cyano, halo, $C_{3-7}$cycloalkyl, $C_{1-6}$alkylcarbonyl, carboxyl, $C_{1-6}$alkyloxycarbonyl, amino, mono- or disubstituted amino, aminocarbonyl, mono- or disubstituted aminocarbonyl, wherein the substituents on any of the amino groups are each individually selected from phenyl, $C_{1-6}$alkyl, $C_{2-6}$alkenyl, $C_{3-7}$cycloalkyl, pyrrolidinyl, piperidinyl, homopiperidinyl or piperazinyl optionally substituted with $C_{1-6}$alkyl; even more in particular wherein Het is a heterocycle selected from the group consisting of pyridinyl, pyrimidinyl, pyrazinyl, pyridazinyl, triazinyl, pyranyl, pyrrolyl, furanyl, thienyl, oxazolyl, isoxazolyl, thiazolyl, isothiazolyl, imidazolyl, tetrahydrofuranyl, tetrahydrothienyl, imidazolinyl, dioxolanyl, pyrrolidinyl, piperidinyl, homopiperidinyl, piperazinyl, homopiperazinyl, dioxanyl, morpholinyl, thiomorpholinyl, which heterocycle may optionally be substituted by $C_{1-6}$alkyl.

Further interesting compounds are those compounds of formula (I) or any subgroup thereof wherein Het is a heterocycle selected from the group consisting of pyridinyl, furanyl, thienyl, tetrahydrofuranyl, pyrrolidinyl, piperidinyl, which heterocycle may optionally be substituted by one, or where possible, more than one substituent selected from the group consisting of $C_{1-6}$alkyl, polyhalo$C_{1-6}$alkyl, $C_{1-6}$alkyloxy, $C_{1-6}$alkylthio, $C_{1-6}$alkylsulfonyl, nitro, cyano, halo, $C_{3-7}$cycloalkyl, $C_{1-6}$alkylcarbonyl, carboxyl, $C_{1-6}$alkyloxycarbonyl, amino, mono- or disubstituted amino, aminocarbonyl, mono- or disubstituted aminocarbonyl, wherein the substituents on any of the amino groups are each individually selected from phenyl, $C_{1-6}$alkyl, $C_{2-6}$alkenyl, $C_{3-7}$cycloalkyl, pyrrolidinyl, piperidinyl, homopiperidinyl or piperazinyl optionally substituted with $C_{1-6}$alkyl; in particular wherein Het is a heterocycle selected from the group consisting of pyridinyl, furanyl, thienyl, tetrahydrofuranyl, pyrrolidinyl, piperidinyl, which heterocycle may optionally be substituted by $C_{1-6}$alkyl.

Suitable subgroups of compounds are those compounds of formula (I) where one or more of the following restrictions apply:
  a) a is zero or 1;
  b) $R^1$ is $C_{1-10}$alkyl, $C_{3-12}$cycloalkyl, Het, aryl or $C_{1-10}$alkyl substituted with a substituent selected from the group consisting of Het, aryl, $C_{3-12}$cycloalkyl and mono- or disubstituted amino wherein the substituents on the amino group are each individually selected from $C_{1-10}$alkyl;
  c) $R^2$ is hydrogen, $C_{1-10}$alkyl, $C_{2-10}$alkenyl or $C_{1-10}$alkyl substituted with aryl;
  d) $R^1$ and $R^2$ taken together with the nitrogen atom to which they are attached form a 5 to 12 membered saturated or partially saturated heterocycle which heterocycle may optionally be substituted with $C_{1-10}$alkyl, $C_{1-6}$alkyloxycarbonyl or $C_{1-10}$alkyl substituted with aryl;
  e) L is $C_{1-2}$alkanediyl;
  f) $R^3$ is halogen, nitro, $C_{1-10}$alkyl, $C_{3-12}$cycloalkyl, polyhalo$C_{1-10}$alkyl, cyano, $C_{1-10}$alkyloxy, $C_{1-10}$alkylthio, $C_{1-10}$alkylsulfonyl, piperidinyl, morpholinyl;
  g) aryl is phenyl optionally substituted with one or more substituents selected from the group consisting of $C_{1-10}$alkyloxy, halo, mono- or disubstituted amino, wherein the substituents on any of the amino groups are each individually selected from $C_{1-10}$alkyl;
  h) Het is a 5 or 6 membered aromatic, saturated or partially saturated, monocyclic or bicyclic heterocycle with one or more heteroatoms each individually selected from nitrogen, oxygen or sulfur, and which heterocycle may optionally be substituted by $C_{1-10}$alkyl.

Particular compounds are those compounds of formula (I) or any subgroup thereof, such as the interesting compounds defined above, wherein the —C(=O)—NR$^1$R$^2$ moiety is in the para position on the phenyl ring which is linked to the 2-position of the 1,9b-dihydro-5-oxa-3,3a-diaza-cyclopenta[a]naphthalene scaffold (also named 1,10b-dihydro-5H-pyrazolo[1,5-c][1,3]benzoxazine scaffold) as depicted in the figure below by the compound of formula (Ia)

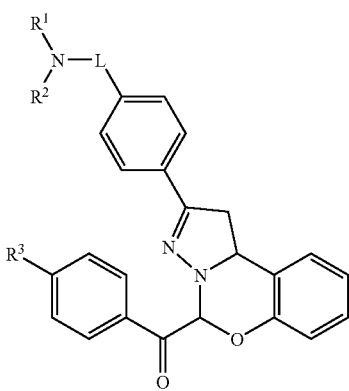

Other particular compounds are those compounds of formula (I) or any subgroup thereof, such as the interesting compounds defined above, wherein a is zero or 1 and R$^3$ is halogen, nitro, C$_{1-10}$alkyl, C$_{3-12}$cycloalkyl, polyhaloC$_{1-10}$alkyl, cyano, C$_{1-10}$alkyloxy, C$_{1-10}$alkylthio, C$_{1-10}$alkylsulfonyl, piperidinyl, morpholinyl.

Other particular compounds are those compounds of formula (I) or (Ia) or any subgroup thereof, such as the interesting compounds defined above, wherein R$^1$ is C$_{1-10}$alkyl, C$_{3-12}$cycloalkyl, Het, aryl or C$_{1-10}$alkyl substituted with a substituent selected from the group consisting of Het, aryl, C$_{3-12}$cycloalkyl and mono- or disubstituted amino wherein the substituents on the amino group are each individually selected from C$_{1-10}$alkyl; R$^2$ is hydrogen, C$_{1-10}$alkyl, C$_{2-10}$alkenyl or C$_{1-10}$alkyl substituted with aryl; or R$^1$ and R$^2$ taken together with the nitrogen atom to which they are attached form a 5 to 12 membered saturated or partially saturated heterocycle which heterocycle may optionally be substituted with C$_{1-10}$alkyl, C$_{1-6}$alkyloxycarbonyl or C$_{1-10}$alkyl substituted with aryl.

Preferred compounds are those compounds of formula (I) or (Ia) or any subgroup thereof, such as the interesting and particular compounds defined above, wherein
a is zero or 1;
R$^1$ is C$_{1-10}$alkyl, C$_{3-12}$cycloalkyl, Het, aryl or C$_{1-10}$alkyl substituted with a substituent selected from the group consisting of Het, aryl, C$_{3-12}$cycloalkyl and mono- or disubstituted amino wherein the substituents on the amino group are each individually selected from C$_{1-10}$alkyl;
R$^2$ is hydrogen, C$_{1-10}$alkyl, C$_{2-10}$alkenyl or C$_{1-10}$alkyl substituted with aryl; or
R$^1$ and R$^2$ taken together with the nitrogen atom to which they are attached form a 5 to 12 membered saturated or partially saturated heterocycle which heterocycle may optionally be substituted with C$_{1-10}$alkyl, C$_{1-6}$alkyloxycarbonyl or C$_{1-10}$alkyl substituted with aryl;
R$^3$ is halogen, nitro, C$_{1-10}$alkyl, C$_{3-12}$cycloalkyl, polyhaloC$_{1-10}$alkyl, cyano, C$_{1-10}$alkyloxy, C$_{1-10}$alkylthio, C$_{1-10}$alkylsulfonyl, piperidinyl, morpholinyl.

Other preferred compounds are those compounds of formula (I) or (Ia) or any subgroup thereof, such as the interesting and particular compounds defined above, wherein
a is zero or 1;
R$^1$ is C$_{1-10}$alkyl, C$_{3-12}$cycloalkyl, Het, aryl or C$_{1-10}$alkyl substituted with a substituent selected from the group consisting of Het, aryl, C$_{3-12}$cycloalkyl and mono- or disubstituted amino wherein the substituents on the amino group are each individually selected from C$_{1-10}$alkyl;
R$^2$ is hydrogen, C$_{1-10}$alkyl, C$_{2-10}$alkenyl or C$_{1-10}$alkyl substituted with aryl; or
R$^1$ and R$^2$ taken together with the nitrogen atom to which they are attached form a 5 to 12 membered saturated or partially saturated heterocycle which heterocycle may optionally be substituted with C$_{1-10}$alkyl, C$_{1-6}$alkyloxycarbonyl or C$_{1-10}$alkyl substituted with aryl;
R$^3$ is halogen, nitro, C$_{1-10}$alkyl, C$_{3-12}$cycloalkyl, polyhaloC$_{1-10}$alkyl, cyano, C$_{1-10}$alkyloxy, C$_{1-10}$alkylthio, C$_{1-10}$alkylsulfonyl, piperidinyl, morpholinyl;
aryl is phenyl optionally substituted with one or more substituents selected from the group consisting of C$_{1-10}$alkyloxy, halo, mono- or disubstituted amino, wherein the substituents on any of the amino groups are each individually selected from C$_{1-10}$alkyl;
Het is a 5 or 6 membered aromatic, saturated or partially saturated, monocyclic or bicyclic heterocycle with one or more heteroatoms each individually selected from nitrogen, oxygen or sulfur, and which heterocycle may optionally be substituted by C$_{1-10}$alkyl.

More preferred compounds are those compounds of formula (I) or (Ia) or any subgroup thereof, such as the interesting and particular compounds defined above, wherein
a is zero or 1;
R$^1$ is C$_{1-6}$alkyl, C$_{3-7}$cycloalkyl, Het, aryl or C$_{1-6}$alkyl substituted with a substituent selected from the group consisting of Het, aryl, C$_{3-7}$cycloalkyl and mono- or disubstituted amino wherein the substituents on the amino group are each individually selected from C$_{1-6}$alkyl;
R$^2$ is hydrogen, C$_{1-6}$alkyl, C$_{2-6}$alkenyl, or C$_{1-6}$alkyl substituted with a substituent selected from the group consisting of aryl or
R$^1$ and R$^2$ taken together with the nitrogen atom to which they are attached form a heterocycle selected from the group consisting of piperazinyl, homopiperazinyl, piperidinyl, homopiperidinyl, morpholinyl, thiomorpholinyl, pyrrolidinyl, indolinyl, 1,2,3,4-tetrahydroquinolinyl, 1,2,3,4-tetrahydro-isoquinolinyl, which heterocycle may optionally be substituted with C$_{1-6}$alkyl, C$_{1-6}$alkyloxycarbonyl or C$_{1-6}$alkyl substituted with aryl;
R$^3$ is halogen, nitro, C$_{1-6}$alkyl, C$_{3-7}$cycloalkyl, polyhaloC$_{1-4}$alkyl, cyano, C$_{1-6}$alkyloxy, C$_{1-6}$alkylthio, C$_{1-6}$alkylsulfonyl, piperidinyl, morpholinyl;
aryl is phenyl optionally substituted with one, two or three substituents selected from the group consisting of C$_{1-6}$alkyl, C$_{1-6}$alkyloxy, nitro, cyano, halo, amino, mono- or disubstituted amino, wherein the substituents on any of the amino groups are each individually selected from C$_{1-6}$alkyl;
Het is a heterocycle selected from the group consisting of pyridinyl, furanyl, thienyl, tetrahydrofuranyl, pyrrolidinyl, piperidinyl, which heterocycle may optionally be substituted by C$_{1-6}$alkyl.

Other more preferred compounds are the compounds of formula (I) or (Ia) or any subgroup thereof, such as the interesting, particular and preferred compounds defined above, wherein $R^2$ is hydrogen and $R^3$ is cyano.

Other more preferred compounds are the compounds of formula (I) or any subgroup thereof, such as the interesting, particular and preferred compounds defined above, wherein a is 1 and $R^3$ is halogen, cyano, $C_{1-4}$alkyl, $C_{1-4}$alkylthio; morpholinyl, $C_{1-4}$alkyloxy, nitro, $C_{1-4}$alkylsulfonyl, trifluoromethyl.

Most preferred compounds include

4-[2-(4-Diethylaminomethyl-phenyl)-1,9b-dihydro-5-oxa-3,3a-diaza-cyclopenta[a]-naphthalene-4-carbonyl]-benzonitrile;

4-{2-[4-(Benzylamino-methyl)-phenyl]-1,9b-dihydro-5-oxa-3,3a-diaza-cyclopenta[a]-naphthalene-4-carbonyl}-benzonitrile;

4-[2-(4-{[(Pyridin-4-ylmethyl)-amino]-methyl}-phenyl)-1,9b-dihydro-5-oxa-3,3a-diaza-cyclopenta[a]naphthalene-4-carbonyl]-benzonitrile;

4-[2-(4-{[(4-Methoxy-benzyl)-methyl-amino]-methyl}-phenyl)-1,9b-dihydro-5-oxa-3,3a-diaza-cyclopenta[a]naphthalene-4-carbonyl]-benzonitrile;

(4-tert-Butyl-phenyl)-[2-(4-{[(4-methoxy-benzyl)-methyl-amino]-methyl}-phenyl)-1,9b-dihydro-5-oxa-3,3a-diaza-cyclopenta[a]naphthalen-4-yl]-methanone;

(4-tert-Butyl-phenyl)-[2-(4-{[(pyridin-4-ylmethyl)-amino]-methyl}-phenyl)-1,9b-dihydro-5-oxa-3,3a-diaza-cyclopenta[a]naphthalen-4-yl]-methanone;

(4-tert-Butyl-phenyl)-[2-(4-diethylaminomethyl-phenyl)-1,9b-dihydro-5-oxa-3,3a-diaza-cyclopenta[a]naphthalen-4-yl]-methanone;

4-{2-[4-(2-Diethylamino-ethyl)-phenyl]-1,9b-dihydro-5-oxa-3,3a-diaza-cyclopenta[a]-naphthalene-4-carbonyl}-benzonitrile;

4-(2-{4-[(Cyclopentyl-methyl-amino)-methyl]-phenyl}-1,9b-dihydro-5-oxa-3,3a-diaza-cyclopenta[a]naphthalene-4-carbonyl)-benzonitrile;

4-(2-{4-[4-(4-Methoxy-phenylamino)-butyl]-phenyl}-1,9b-dihydro-5-oxa-3,3a-diaza-cyclopenta[a]naphthalene-4-carbonyl)-benzonitrile;

(4-Methanesulfonyl-phenyl)-[2-(4-{[(pyridin-4-ylmethyl)-amino]-methyl}-phenyl)-1,9b-dihydro-5-oxa-3,3a-diaza-cyclopenta[a]naphthalen-4-yl]-methanone;

(4-Methanesulfonyl-phenyl)-[2-(4-{[(4-methoxy-benzyl)-methyl-amino]-methyl}-phenyl)-1,9b-dihydro-5-oxa-3,3a-diaza-cyclopenta[a]naphthalen-4-yl]-methanone;

[2-(4-Diethylaminomethyl-phenyl)-1,9b-dihydro-5-oxa-3,3a-diaza-cyclopenta[a]-naphthalen-4-yl]-(4-methanesulfonyl-phenyl)-methanone;

and the N-oxides, stereoisomeric forms and salts thereof.

Due to the fact that the compounds of formula (I) are inhibitors of the replication of HIV, the compounds of formula (I) are useful in the treatment of warm-blooded animals, in particular humans, infected with HIV. Conditions associated with HIV which may be prevented or treated with the compounds of the present invention include AIDS, AIDS-related complex (ARC), progressive generalized lymphadenopathy (PGL), as well as chronic CNS diseases caused by retroviruses, such as, for example HIV mediated dementia and multiple sclerosis.

The compounds of the present invention may therefore be used as medicines. The compounds of the present invention may be used in the manufacture of a medicament useful for treating conditions associated with HIV infection.

The compounds of the present invention may also be used against or in a method of treating above-mentioned conditions. Said method of treatment comprises the systemic administration of an effective therapeutic amount of a compound of formula (I) to HIV-infected warm-blooded animals, in particular HIV-infected humans.

In one embodiment, the invention relates to the use of the compounds of the present invention in the manufacture of a medicament for preventing HIV transmission or HIV infection or disease associated with HIV infection of warm-blooded animals, in particular humans, and in particular transmission or infection via sexual intercourse or related intimate contact between partners. Thus, the invention also relates to a method of preventing HIV transmission or HIV infection or a disease associated with HIV infection comprising administering to a warm-blooded animal, in particular a human, an effective preventive amount of a compound of formula (I), and in particular transmission or infection via sexual intercourse or related intimate contact between partners.

The favourable properties of the present compounds with respect to their ability to inhibit HIV viral replication can be demonstrated using an anti-viral replication assay that directly measures the ongoing replication of a wild-type HIV virus in MT4 cells via the specific interaction of HIV-tat with LTR sequences coupled to GFP (MT4-LTR-EGFP cells). It has also been found, using the above anti-viral replication assay, that the present compounds inhibit the replication a panel of reverse transcriptase resistant viruses, protease resistant viruses or combined reverse transcriptase and protease resistant viruses (so-called multi-drug resistant viruses).

The present compounds were tested in a time of addition experiment. Time of addition experiments provide an indication at what time point a test compound inhibits the viral replication in a cellular environment. In particular, test compounds of the present invention were added at different time intervals to HIV-1 infected MT4 cells expressing HIV-1-LTR-luciferase reporter gene (MT4-LTR-Luc) or MT4 cells expressing HIV-1-LTR-EGFP reporter gene (MT4-LTR-EGFP). The first time point for addition of a test compound was 30 minutes post virus synchronisation.

The present compounds were also tested in an entry reporter assay (ERA) that measures inhibition of cell-cell fusion between cell line persistently expressing HIV (effector cell line) and a cell line expressing CD4 and CXCR4 (target cell line) equipped with LTR-EGFP using FACS read-out.

A toxicity assay wherein a reduced expression of the GFP reporter protein (MT4-CMV-EGFP cells) serves as a marker for cellular toxicity of a test compound can be used to measure the toxicity of the present compounds.

In general, the compounds of the present invention can be obtained by the synthetic sequence depicted in Scheme 1.

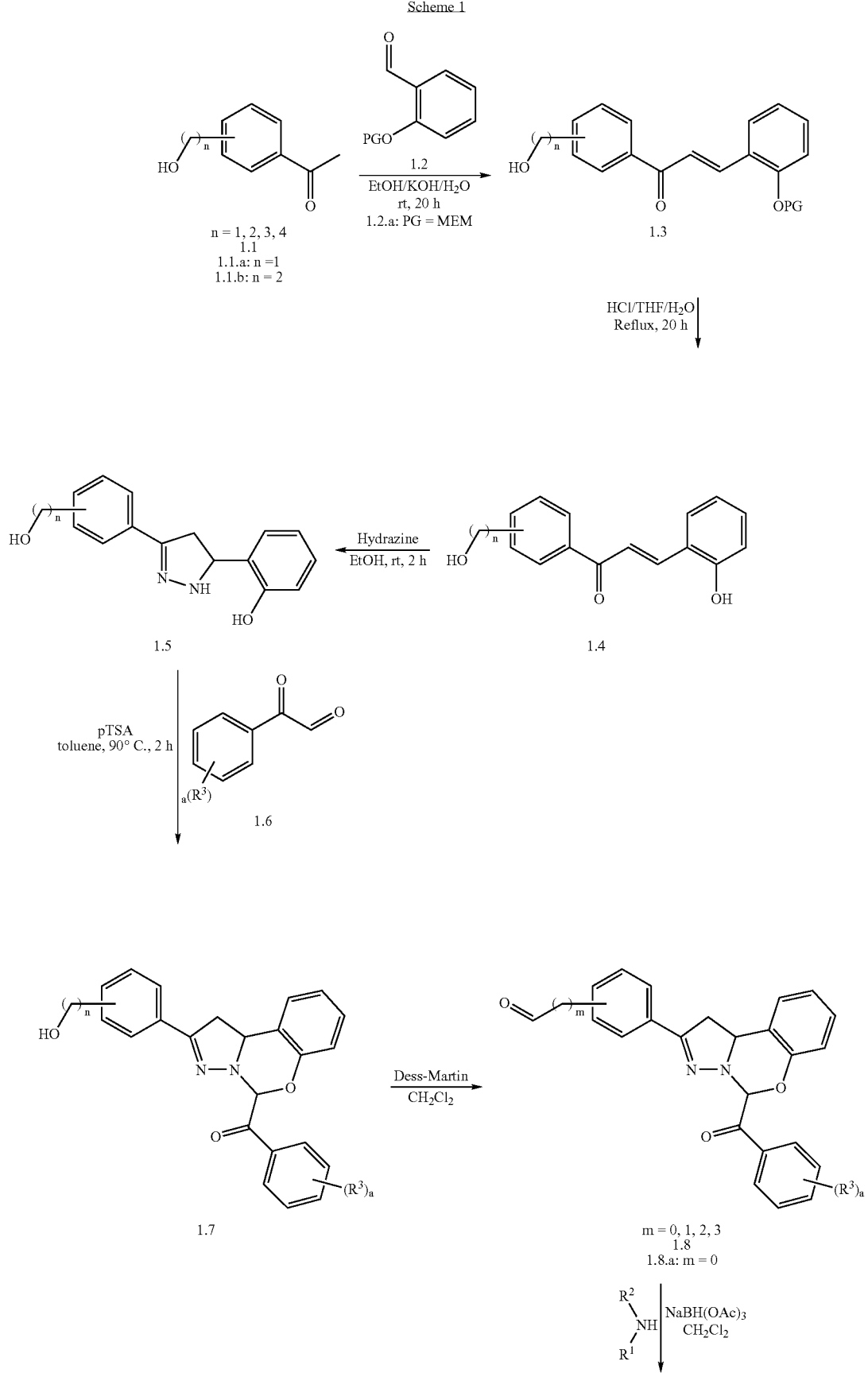

-continued

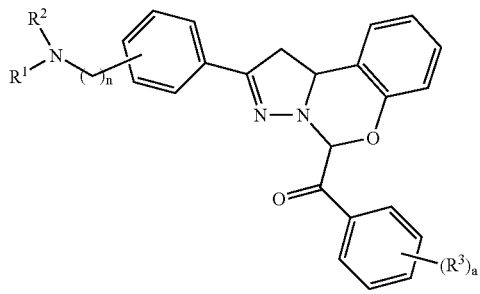

1.9

In scheme 1, the intermediates of formula 1.1 can be condensed with a salicylaldehyde of formula 1.2 in the presence of a suitable base, such as a mineral base like potassium hydroxide or sodium hydroxide, in a suitable solvent system such as for instance a mixture of an alcohol and water, e.g. a mixture of ethanol and water. Alternatively, an organic base such as pyrrolidine in a suitable solvent such as tetrahydrofuran or dichloromethane can be used. The variable "PG" in intermediate 1.2 is meant to be a protecting group for the hydroxyl group such as for instance methoxymethyl, tert-butoxymethyl, tetrahydropyranyl or methoxyethoxymethyl (MEM). Scheme 3 below depicts the reaction procedure to prepare an intermediate of formula 1.2 wherein the protecting group is MEM. The resulting intermediate of the above condensation reaction in Scheme 1 is a chalcone of formula 1.3 (also described in J. Med. Chem., 2000, 43, 4868-4876). The protected chalcone of formula 1.3 can be deprotected in acidic media for instance by using hydrochloric acid in an appropriate solvent such as for example tetrahydrofuran, dichloromethane or an alcohol, thus yielding an intermediate of formula 1.4. Intermediate 1.4 can then be further reacted with hydrazine in a suitable water-miscible solvent such as for instance dioxane, toluene or an alcohol like ethanol, to yield the dihydropyrazol of formula 1.5 (J. Ind. Chem. Soc., 1989, 66, 893-896). The compound of formula 1.7 can then be prepared via the coupling of the dihydropyrazol of formula 1.5 with an appropriate glyoxal of formula 1.6 in a suitable solvent such as toluene or dioxane, and in the presence of a catalytic amount of an acid such as para-toluenesulfonic acid. Intermediate 1.7 can be oxidized with a Dess-Martin reagent or another oxidant known in the art of chemistry such as Swern conditions in a suitable solvent such as dichloromethane or hexane to get the aldehyde 1.8. The desired amines 1.9 can then be prepared via the reductive amination of the aldehyde 1.8 using sodium triacetoxyborohydride or sodium cyanoborohydride in a suitable solvent such as dichloromethane, dichloroethane or tetrahydrofuran (THF).

Scheme 2

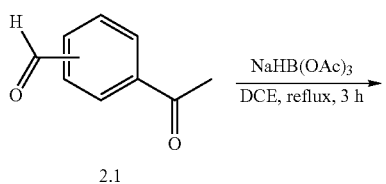
2.1

-continued

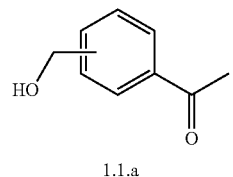
1.1.a

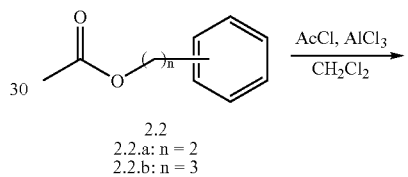
2.2
2.2.a: n = 2
2.2.b: n = 3

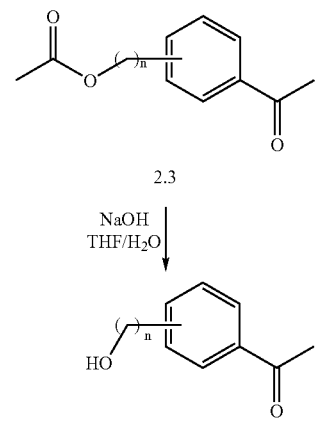
2.3 n = 2, 3, 4

In scheme 2, compound of formula 1.1.a, which is used as starting material in scheme 1, can be prepared via the commercially available acetylbenzaldehyde using a reducing agent such as sodium triacetoxyborohydride in a suitable solvent such as dichloroethane.

Also in scheme 2, compound of formula 1.1.b can be prepared via Friedel-Crafts acylation of the acetate 2.2.a using Lewis acid reagent such as aluminium chloride or boron tribromide in a suitable solvent such as dichloromethane, ether or hexane followed with the hydrolysis of the ester 2.3 giving the desired compound 1.1.b.

Scheme 3

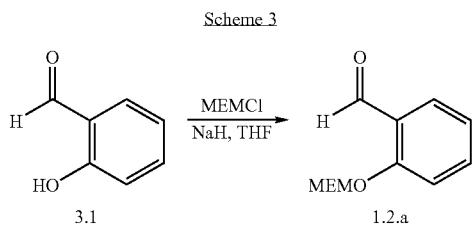

The preparation of intermediate of formula 1.2.a with MEM as protecting group can be obtained by reacting salicylaldehyde 3.1, which is commercially available, with chloromethoxymethoxy ethane in the presence of a base such as sodium hydride or potassium hydride, and in the presence of suitable solvent like N,N-dimethylformamide or tetrahydrofuran.

Scheme 4

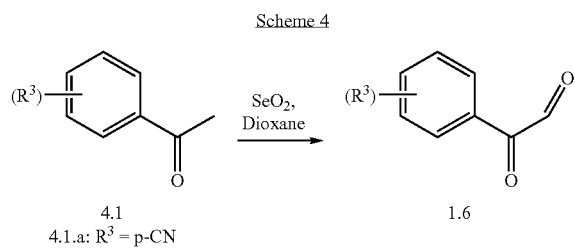

4.1
4.1.a: $R^3$ = p-CN

The preparation of a glyoxal of formula 1.6 can be carried out starting from an intermediate of formula 4.1 in a manner or analogous to a manner described in J. Het. Chem. 1987, 24, 441-451. More in particular, the acetyl of formula 4.1 can be oxidized to a glyoxal of formula 1.6 in a solvent such as dioxane using selenium oxide as oxidating agent.

In preparations presented above, the reaction products may be isolated from the reaction medium and, if necessary, further purified according to methodologies generally known in the art such as, for example, extraction, crystallization, distillation, trituration and chromatography.

The compounds of formula (I) as prepared in the hereinabove described processes may be synthesized as a mixture of stereoisomeric forms, in particular in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of the present invention can thus be used in animals, preferably in mammals, and in particular in humans as pharmaceuticals per se, in mixtures with one another or in the form of pharmaceutical preparations.

Furthermore, the present invention relates to pharmaceutical preparations which as active constituents contain an effective dose of at least one of the compounds of formula (I) in addition to customary pharmaceutically innocuous excipients and auxiliaries. The pharmaceutical preparations normally contain 0.1 to 90% by weight of the compound. The pharmaceutical preparations can be prepared in a manner known per se to one of skill in the art. For this purpose, at least one of a compound of the present invention, together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals which contain a compound according to the invention can be administered orally, parenterally, e.g., intravenously, rectally, by inhalation, or topically, the preferred administration being dependent on the individual case, e.g., the particular course of the disorder to be treated. Oral administration is preferred.

The person skilled in the art is familiar on the basis of his expert knowledge with the auxiliaries which are suitable for the desired pharmaceutical formulation. Beside solvents, gel-forming agents, suppository bases, tablet auxiliaries and other carriers for compounds, antioxidants, dispersants, emulsifiers, antifoams, flavor corrigents, preservatives, solubilizers, agents for achieving a depot effect, buffer substances or colorants are also useful.

The compounds of the present invention may also find use in inhibiting ex vivo samples containing HIV or expected to be exposed to HIV. Hence, the present compounds may be used to inhibit HIV present in a body fluid sample which contains or is suspected to contain or be exposed to HIV.

Also, the combination of an antiretroviral compound and a compound of the present invention can be used as a medicine. Thus, the present invention also relates to a product containing (a) a compound of the present invention, and (b) another antiretroviral compound, as a combined preparation for simultaneous, separate or sequential use in treatment of retroviral infections. Thus, to combat or treat HIV infections, or the infection and disease associated with HIV infections, such as Acquired Immunodeficiency Syndrome (AIDS) or AIDS Related Complex (ARC), the compounds of this invention may be co-administered in combination with for instance, binding inhibitors, such as, for example, dextran sulfate, suramine, polyanions, soluble CD4, gp120 binder such as BMS378806, anti CD4 Ab compounds such as PRO-542 or TNX-355; fusion inhibitors, such as, for example, T20, T1249, co-receptor binding inhibitors, such as, for example, AK-602, SCH-C, SCH-D, AMD 3100 (Bicyclams), AMD-070, TAK 779, TAK 220, UK-427-857, PRO-140; RT inhibitors, such as, for example, foscarnet and prodrugs; nucleoside RTIs, such as, for example, AZT, 3TC, DDC, DDI, D4T, Abacavir, FTC, Emtricitabine, DAPD, dOTC; nucleotide RTIs, such as, for example, PMEA, PMPA, tenofovir; NNRTIs, such as, for example, nevirapine, delavirdine, efavirenz, tivirapine, loviride, etravirine, dapivirine, rilpivirine, TMC120, TMC125, MKC-442, UC 781, Capravirine, DPC 961, DPC963, DPC082, DPC083, calanolide A, SJ-3366, TSAO, 4"-deaminated TSAO; RNAse H inhibitors, such as, for example, SP1093V, PD126338; TAT inhibitors, such as, for example, RO-5-3335, K12, K37; integrase inhibitors, such as, for example, L 708906, L 731988; protease inhibitors, such as, for example, darunavir, amprenavir, ritonavir, nelfinavir, saquinavir, indinavir, lopinavir, lasinavir, atazanavir, BMS 186316, DPC 681, DPC 684, tipranavir, AG1776, DMP 450, L 756425, PD178390, PNU 140135; glycosylation inhibitors, such as, for example, castanospermine, deoxynojirimycine.

Of particular interest are products comprising (i) a compound of formula (I), and (ii) darunavir, and a booster such as ritonavir as a combined preparation for simultaneous, separate or sequential use in treatment of retroviral infections.

Of particular interest are products comprising (i) a compound of formula (I), and (ii) etravirine, as a combined preparation for simultaneous, separate or sequential use in treatment of retroviral infections.

Of particular interest are products comprising (i) a compound of formula (I), and (ii) dapivirine, as a combined preparation for simultaneous, separate or sequential use in treatment of retroviral infections.

Of particular interest are products comprising (i) a compound of formula (I), and (ii) rilpivirine, as a combined preparation for simultaneous, separate or sequential use in treatment of retroviral infections.

The compounds of the present invention may also be administered in combination with immunomodulators (e.g., bropirimine, anti-human alpha interferon antibody, IL-2, methionine enkephalin, interferon alpha, and naltrexone) or with antibiotics (e.g., pentamidine isothiorate) to ameliorate, combat, or eliminate HIV infection and its symptoms.

For an oral administration form, compounds of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the active compounds, if desired with the substances customary therefor such as solubilizers, emulsifiers or further auxiliaries, are brought into solution, suspension, or emulsion. The compounds can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compounds or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

In order to enhance the solubility and/or the stability of the compounds in pharmaceutical compositions, it can be advantageous to employ α-, β- or γ-cyclo-dextrins or their derivatives. Also co-solvents such as alcohols may improve the solubility and/or the stability of the compounds in pharmaceutical compositions. In the preparation of aqueous compositions, addition salts of the subject compounds are obviously more suitable due to their increased water solubility.

Appropriate cyclodextrins are α-, β- or γ-cyclodextrins (CDs) or ethers and mixed ethers thereof wherein one or more of the hydroxy groups of the anhydroglucose units of the cyclodextrin are substituted with alkyl, particularly methyl, ethyl or isopropyl, e.g. randomly methylated β-CD; hydroxyalkyl, particularly hydroxyethyl, hydroxy-propyl or hydroxybutyl; carboxyalkyl, particularly carboxymethyl or carboxyethyl; alkylcarbonyl, particularly acetyl; alkyloxycarbonylalkyl or carboxyalkyloxyalkyl, particularly carboxymethoxypropyl or carboxyethoxypropyl; alkylcarbonyloxyalkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)-propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

An interesting way of formulating the present compounds in combination with a cyclodextrin or a derivative thereof has been described in EP-A-721,331. Although the formulations described therein are with antifungal active ingredients, they are equally interesting for formulating the compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. Said formulations may also be rendered more palatable by adding pharmaceutically acceptable sweeteners and/or flavors.

Other convenient ways to enhance the solubility of the compounds of the present invention in pharmaceutical compositions are described in WO-94/05263, PCT application No. PCT/EP98/01773, EP-A-499299, WO 97/44014, and WO 01/22938 all incorporated herein by reference.

More in particular, the present compounds may be formulated in a pharmaceutical composition comprising a therapeutically effective amount of particles consisting of a solid dispersion comprising (a) a compound of the present invention, and (b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion is referred to as "a solid solution". Solid solutions are preferred physical systems because the components therein are usually readily bioavailable to the organisms to which they are administered.

The term "a solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2% aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation.

It may further be convenient to formulate the present compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition whereby the compounds of this invention are incorporated in hydrophilic polymers and applying this mixture as a coat film over many small beads, thus yielding a composition with good bioavailability which can conveniently be manufactured and which is suitable for preparing pharmaceutical dosage forms for oral administration.

Said beads comprise (a) a central, rounded or spherical core, (b) a coating film of a hydrophilic polymer and an antiretroviral agent and (c) a seal-coating polymer layer. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

Another aspect of the present invention concerns a kit or container comprising a compound of the present invention, in an amount effective for use as a standard or reagent in a test or assay for determining the ability of a potential pharmaceutical to inhibit HIV entry, HIV growth, or both. This aspect of the invention may find its use in pharmaceutical research programs.

The dose of the present compounds or of the physiologically tolerable salt(s) thereof to be administered depends on the individual case and, as customary, is to be adapted to the conditions of the individual case for an optimum effect. Thus it depends, of course, on the frequency of administration and on the potency and duration of action of the compounds employed in each case for therapy or prophylaxis, but also on the nature and severity of the infection and symptoms, and on the sex, age, weight and individual responsiveness of the human or animal to be treated and on whether the therapy is acute or prophylactic. Customarily, the daily dose of a compound of the present invention, in the case of administration to a patient approximately 75 kg in weight ranges between 1 mg and 5 g, preferably between 10 mg and 2 g, more preferably between 20 mg and Ig. The dose can be administered in the form of an individual dose, or divided into several, e.g. two, three, four or even more, individual doses.

EXPERIMENTAL PART

Example 1

Synthesis of 4-[4-(4-cyano-benzoyl)-1,9b-dihydro-5-oxa-3,3a-diaza-cyclopenta[a]naphthalen-2-yl]-N,N-diethyl-benzylamine 1.9.a (Compound 1)

Synthesis of 4-hydroxymethyl-benzophenone 1.1.a

To a solution of 4-acetylbenzaldehyde (9 g, 61 mmol) in 1,2-dichloroethylene (1,2-DCE) (100 ml), $NaHB(OAc)_3$ or sodium triacetoxyborohydride (19.3 g, 90 mmol) was added and the reaction mixture was refluxed for 7 hours. Then, the mixture was poured out on $NH_4Cl$ (sat, aq) and extracted with $CH_2Cl_2$ (3×50 ml). The combined organic layers were washed with brine, dried ($Na_2SO_4$) and concentrated. The product was purified by column chromatography (ethyl acetate/heptane=70/30) to give 8.08 g of product 1.1.a (89% yield).

Synthesis of Compound 2.3.a

To a solution of compound 2.2.a (20 ml, 112 mmol) in $CH_2Cl_2$ (1000 ml) was added aluminium chloride (14.9 g, 112 mmol) and mixture was cooled to 0° C. Then, a solution of acetyl chloride (8 ml, 112 mmol) in $CH_2Cl_2$ was added dropwise while maintaining the temperature below 0° C. Then, another equivalent of aluminium chloride was added and the mixture was stirred at 0° C. for 1.5 hours. The mixture was poured into ice-water and ~20 ml of conc. HCl was added. The organic layer was separated, washed with brine, dried ($Na_2SO_4$) and concentrated. The resulting oil was purified by column chromatography (ethyl acetate/heptane=1/1), to give 12.1 g of 2.3.b (49% yield).

Synthesis of Compound 1.1.b

Compound 2.3.a (12.1 g, 55 mmol) was dissolved in THF/water (400 ml, 1/1) and sodium hydroxide (2.3 g, 57 mmol) was added. The reaction mixture was stirred at room temperature for 6 hours. Then, the THF layer separated and the water layer extracted with $Et_2O$ or diethyl ether (2×50 ml). The combined organic layers were washed with brine, dried ($Na_2SO_4$) and concentrated to give 1.1.b as a white solid (9.4 g, 96% yield).

Synthesis of 2-(2-methoxy-ethoxymethoxy)-benzaldehyde 1.2

Intermediate 2.1 (20 mmol) was dissolved in THF (150 ml). The resulting mixture was cooled to 0° C. Sodium hydride (30 mmol) was added and the mixture was stirred at room temperature for 1 hour and chloromethoxymethoxy ethane (20 mol) was added. The mixture was stirred at room temperature for 16 hours. Water (200 ml) was added and the mixture was extracted with dichloromethane. The organic layer was separated, dried (over $MgSO_4$), filtered and the solvent was evaporated till dryness. The residue was filtered on silica gel using dichloromethane as eluent. The solvent was removed to yield 95% of compound 1.2.a.

Synthesis of 4-{3-[2-(2-methoxy-ethoxymethoxy)-phenyl]-acryloyl}-benzylalcohol 1.3.a To a solution of compounds 1.1.a (8 g, 53 mmol) and 1.2.a (11.2 g, 53 mmol) in ethanol (350 ml) KOH (5.94 g, 106 mmol) in $H_2O$ (5 ml) was added. The reaction mixture was stirred at rt for 20 hours and subsequently poured out on $NH_4Cl$ (aq, sat.) and extracted with ethylacetate (EtOAc) (3×100 ml). The combined organic layers were washed with brine, dried ($Na_2SO_4$) and concentrated. The product was purified by column chromatography (ethyl acetate/heptane=1/1) to give 15.5 g of product 1.3.a (85% yield, LCMS 90% pure).

Synthesis of 4-[3-(2-hydroxy-phenyl)-acryloyl]-benzylalcohol 1.4.a

Compound 1.3.a (15.5 g, 45 mmol) was dissolved in THF (350 ml) and 1M HCl (95 ml) was added. The reaction mixture was refluxed for 20 hours, after which the solvent was evaporated. Then, $CH_2Cl_2$ (50 ml) was added and the organic layer was extracted twice with 1M NaOH (100 ml). The combined NaOH layers were acidified using 1M HCl and the product precipitated from the solution. The product was filtrated off and dried in a vacuum stove to give 9.3 g of product 1.4.a (81% yield).

Synthesis of 4-[5-(2-hydroxy-phenyl)-4,5-dihydro-1H-pyrazol-3-yl]-benzylalcohol 1.5.a Compound 1.4.a (9.3 g, 37 mmol) was dissolved in ethanol (EtOH) (350 mL) and hydrazine (7.3 g, 146 mmol) was added in one portion. The reaction mixture was stirred for 2 hours at room temperature. The product precipitated from the solution and was filtrated off and dried in a vacuum stove, to give 6.2 g of product 1.5.a (63% yield).

Synthesis of 4-(2-oxo-acetyl)-benzonitrile 1.6.a

To a solution of 4-cyanoacetophenone 4.1.a (6 g, 41 mmol) in dioxane (250 mL), selenium dioxide (9.1 g, 82 mmol) was added. The reaction mixture was refluxed for 20 hours, cooled to room temperature, filtrated and concentrated. The residue was dissolved in $CH_2Cl_2$ and filtrated again. The solvent was evaporated and the residue was purified by column chromatography (ethyl acetate/heptane=1/1), to give 5.2 g of glyoxal 1.6.a (80% yield).

Synthesis of 4-[4-(4-cyano-benzoyl)-19b-dihydro-5-oxa-3,3a-diaza-cyclopenta[a]-naphthalen-2-yl]-benzylalcohol 1.7.a Compound 1.5.a (5.5 g, 20 mmol) was placed in toluene (200 mL) and sonicated for 30 minutes. Then, the solution was heated to 80° C. and stirred at that temperature for 30 minutes. Then para-toluene sulfonic acid (0.19 g, 1 mmol) was added. Next, a solution of glyoxal 1.6.a (3.6 g, 23 mmol) in THF (20 mL) was added dropwise and the reaction mixture was stirred at 80° C. for 1.5 hours. After this time the solvent was evaporated and the product was purified by column chromatography ($CH_2Cl_2$/MeOH=99/1) to give 5.3 g of product 1.7.a (63% yield). "MeOH" refers to methanol.

Synthesis of 4-[4-(4-cyano-benzoyl)-1,9b-dihydro-5-oxa-3,3a-diaza-cyclopenta [a]naphthalen-2-yl]-benzaldehyde 1.8.a Compound 1.7.a (2 g, 4.9 mmol) was dissolved in $CH_2Cl_2$ (60 ml) and Dess-Martin Periodinane (14 ml, 15 wt % in $CH_2Cl_2$, 6.83 mmol) was added to the reaction mixture. The reaction mixture was stirred for 4 hours at room temperature. Then $NaHCO_3$ (aq, sat.) and $Na_2S_2O_3$ (1 equiv) was added and mixture was stirred vigorously for 15 minutes. The organic layer was separated, washed with brine, dried ($Na_2SO_4$) and concentrated. The product was purified by column chromatography (ethyl acetate/heptane=30/70) to give 1.22 g of product 1.8.a (61% yield).

Example 2

General Procedure for the Synthesis of Compounds 1.9

To a solution of aldehyde 1.8 and the corresponding amine (1.1 equiv.) in $CH_2Cl_2$ was added $NaHB(OAc)_3$ (1.1 equivalents). The reaction mixture was stirred at room temperature overnight and then poured out on $NaHCO_3$ (aqueous, saturated). The organic layer was separated and the water layer was extracted 2 times with $CH_2Cl_2$. The combined organic layers were washed with brine, dried ($Na_2SO_4$) and concentrated. The products were purified by column chromatography using $CH_2Cl_2$/MeOH. Yields ranging from 20-70%.

The compounds listed in the following table were prepared analogous to the procedures described in examples 1 or 2.

TABLE 1

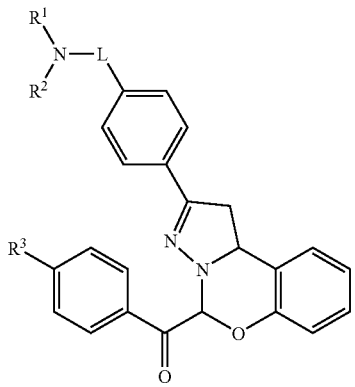

(Ia)

| Compound number | ---NR¹R² | L | R³ |
|---|---|---|---|
| 1 | (diethylamino) | —$CH_2$— | —CN |

TABLE 1-continued
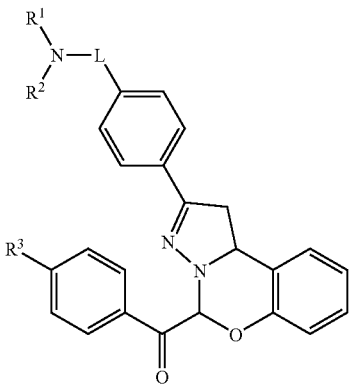
(Ia)
| Compound number | ---NR¹R² | L | R³ |
|---|---|---|---|
| 2 | benzyl-NH--- | —CH₂— | —CN |
| 3 | (pyridin-4-yl)methyl-NH--- | —CH₂— | —CN |
| 4 | (CH₃)₂N-CH₂CH₂-N(CH₃)--- | —CH₂— | —CN |
| 5 | 4-methoxyphenyl-NH--- | —CH₂— | —CN |
| 6 | (pyridin-2-yl)methyl-NH--- | —CH₂— | —CN |
| 7 | pyrrolidin-1-yl-CH₂CH₂-NH--- | —CH₂— | —CN |
| 8 | 4-methoxybenzyl-N(CH₃)--- | —CH₂— | —CN |
| 9 | 4-methoxybenzyl-N(CH₃)--- | —CH₂— | —C(CH₃)₃ |
| 10 | (pyridin-4-yl)methyl-NH--- | —CH₂— | —C(CH₃)₃ |

TABLE 1-continued
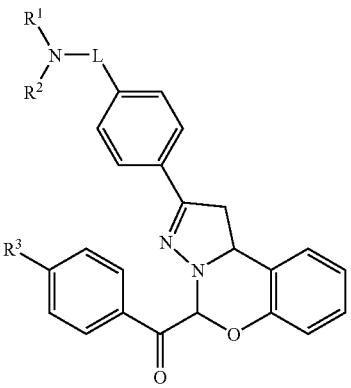
(Ia)
| Compound number | ---NR$^1$R$^2$ | L | R$^3$ |
|---|---|---|---|
| 11 | diethylamino | —CH$_2$— | —C(CH$_3$)$_3$ |
| 12 | diethylamino | —(CH$_2$)$_2$— | —CN |
| 13 | cyclopentyl(methyl)amino | —CH$_2$— | —CN |
| 14 | 4-methoxyphenylamino | —(CH$_2$)$_3$— | —CN |
| 15 | (2-(dimethylamino)ethyl)(methyl)amino | —(CH$_2$)$_3$— | —CN |
| 16 | dimethylamino | —(CH$_2$)$_3$— | —CN |
| 17 | benzylamino | —(CH$_2$)$_3$— | —CN |
| 18 | benzylamino | —(CH$_2$)$_4$— | —CN |
| 19 | diethylamino | —(CH$_2$)$_4$— | —CN |

TABLE 1-continued (Ia)

| Compound number | ---NR¹R² | L | R³ |
|---|---|---|---|
| 20 | 4-methoxyphenyl-NH--- | —(CH₂)₄— | —CN |
| 21 | pyridin-4-yl-CH₂-NH--- | —(CH₂)₄— | —CN |
| 22 | (CH₃)₂N-CH₂-CH₂-N(CH₃)--- | —(CH₂)₄— | —CN |
| 23 | 4-methoxybenzyl-N(CH₃)--- | —(CH₂)₄— | —CN |
| 24 | pyridin-4-yl-CH₂-NH--- | —(CH₂)₃— | —CN |
| 25 | 4-methoxybenzyl-N(CH₃)--- | —(CH₂)₃— | —CN |
| 26 | pyridin-2-yl-CH₂-NH--- | —(CH₂)₄— | —CN |
| 27 | cyclopentyl-N(CH₃)--- | —(CH₂)₄— | —CN |
| 28 | pyridin-3-yl-CH₂-NH--- | —CH₂— | —SO₂—CH₃ |

TABLE 1-continued (Ia)

| Compound number | ---NR¹R² | L | R³ |
|---|---|---|---|
| 29 | 4-methoxybenzyl(methyl)amino | —CH₂— | —SO₂—CH₃ |
| 30 | diethylamino | —CH₂— | —SO₂—CH₃ |
| 31 | (pyridin-2-ylmethyl)amino | —(CH₂)₃— | —CN |
| 32 | 4-methoxybenzyl(methyl)amino | —(CH₂)₂— | —CN |
| 33 | benzylamino | —(CH₂)₂— | —CN |
| 34 | 2-(dimethylamino)ethyl(methyl)amino | —(CH₂)₂— | —CN |
| 35 | cyclopentyl(methyl)amino | —(CH₂)₃— | —CN |
| 36 | 4-(dimethylamino)benzyl(methyl)amino | —CH₂— | —CN |

TABLE 1-continued (Ia)

[Structure: Chemical structure showing the general formula with R¹R²N-L- substituent on a phenyl ring connected to a pyrazoline fused with a benzoxazine system, with R³-substituted phenyl ketone group]

| Compound number | ---NR¹R² | L | R³ |
|---|---|---|---|
| 37 | [4-(dimethylamino)benzyl](methyl)amine group | —CH₂— | —CN |
| 38 | [(pyridin-3-yl)methyl](methyl)amine group | —CH₂— | —CN |

Example 3

Virological Properties of the Compounds of the Present Invention

The compounds were tested in a cellular assay using the MT4-LTR-EGFP cells for anti-viral activity. The assay demonstrated that these compounds exhibit potent anti-HIV activity against a wild type laboratory HIV strain (HIV-1 strain LAI) and a multi-drug resistant HIV-1 virus (HIV-1-MDR). The cellular assay was performed according to the following procedure.

HIV- or mock-infected MT4-LTR-EGFP cells were incubated for three days in the presence of various concentrations of the inhibitor. Upon infection, the GFP reporter is activated by the viral tat protein. At the end of the incubation period, the GFP signal was measured. In the virus control samples (in the absence of any inhibitor) the maximal fluorescent signal was obtained. The inhibitory activity of the compound was monitored on the virus-infected cells and was expressed as $EC_{50}$ and $EC_{90}$. These values represent the amount of the compound required to protect 50% and 90%, respectively, of the cells from virus infection.

TABLE 2

The $pEC_{50}$ values (defined as the negative logarithm of the result expressed as $EC_{50}$) for the tested compounds is shown herein below. For some of the compounds of the present invention, more than one test run was performed. In such a case, the average $pEC_{50}$ value was used to determine the activity class.

| Compound no. | Activity class for HIV-1-LAI test (pEC₅₀ values) | Activity class for HIV-1-MDR test (pEC₅₀ values) |
|---|---|---|
| 1 | 7.72 | 8.06 |
| 2 | 7.58 | 7.83 |
| 3 | 6.88 | 7.08 |
| 4 | 6.41 | 6.25 |
| 5 | 6.22 | 6.5 |
| 6 | 7.13 | 7.28 |
| 7 | 6.55 | 6.49 |
| 8 | 7.81 | 7.85 |
| 9 | 7.28 | 7 |
| 10 | 6.49 | 6.79 |
| 11 | 7.64 | 7.59 |
| 12 | 7.16 | 7.35 |
| 13 | 8.32 | 8.62 |
| 14 | 6.41 | 6.34 |
| 15 | 5.42 | 5.52 |
| 16 | 5.6 | 5.51 |
| 17 | 5.56 | 5.37 |
| 18 | 5.47 | 5.47 |
| 19 | 5.39 | 5.43 |
| 20 | 7.42 | 6.51 |
| 21 | 5.23 | 5.2 |
| 22 | 5.52 | 5.47 |
| 23 | 5.38 | 5.32 |
| 24 | 4.93 | 4.83 |
| 25 | 6.53 | 5.04 |
| 26 | 5.28 | 4.86 |
| 27 | 5.36 | 5.15 |
| 28 | 7.49 | 7.63 |
| 29 | 8.47 | 8.56 |
| 30 | 7.9 | 7.95 |
| 31 | 4.85 | 5.38 |

TABLE 2-continued

The pEC$_{50}$ values (defined as the negative logarithm of the result expressed as EC$_{50}$) for the tested compounds is shown herein below. For some of the compounds of the present invention, more than one test run was performed. In such a case, the average pEC$_{50}$ value was used to determine the activity class.

| Compound no. | Activity class for HIV-1-LAI test (pEC$_{50}$ values) | Activity class for HIV-1-MDR test (pEC$_{50}$ values) |
| --- | --- | --- |
| 32 | 7.08 | 6.72 |
| 33 | 6.35 | 6.07 |
| 34 | 6.25 | 6.12 |
| 35 | 5.76 | 5.81 |
| 36 | 7.45 | 7.18 |
| 37 | 6.12 | 6.31 |

Example 4

Pharmaceutical Compositions

Capsules

Active ingredient, in casu a compound of formula (I), is dissolved in organic solvent such as ethanol, methanol or methylene chloride, preferably, a mixture of ethanol and methylene chloride. Polymers such as polyvinylpyrrolidone copolymer with vinyl acetate (PVP-VA) or hydroxypropylmethylcellulose (HPMC), typically 5 mPa·s, are dissolved in organic solvents such as ethanol, methanol methylene chloride. Suitably the polymer is dissolved in ethanol. The polymer and compound solutions are mixed and subsequently spray dried. The ratio of compound/polymer was selected from 1/1 to 1/6. Intermediate ranges are 1/1.5 and 1/3. A suitable ratio is 1/6. The spray-dried powder, a solid dispersion, is subsequently filled in capsules for administration. The drug load in one capsule ranges between 50 and 100 mg depending on the capsule size used.

Film-Coated Tablets

Preparation of Tablet Core

A mixture of 100 g of active ingredient, in casu a compound of formula (I), 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there was added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methylcellulose in 75 ml of denaturated ethanol there is added a solution of 5 g of ethylcellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated color suspension and the whole is homogenated. The tablet cores are coated with the thus obtained mixture in a coating apparatus.

The invention claimed is:

1. A compound having the formula

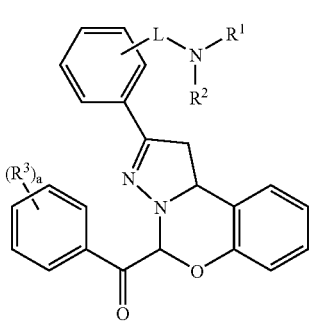

(I)

a N-oxide, stereoisomeric form or salt thereof,
wherein
a is zero, 1, 2, 3, 4 or 5;
L is $C_{1-4}$alkanediyl;
$R^1$ is hydrogen, $C_{1-10}$alkyl, $C_{2-10}$alkenyl, $C_{2-10}$alkynyl, $C_{3-12}$cycloalkyl, Het, aryl or $C_{1-10}$alkyl substituted with a substituent selected from the group consisting of Het, aryl, $C_{3-12}$cycloalkyl, amino and mono- or disubstituted amino wherein the substituents on the amino group are each individually selected from $C_{1-10}$alkyl, $C_{2-10}$alkenyl, $C_{3-12}$cycloalkyl, Het and aryl;
$R^2$ is hydrogen, $C_{1-10}$alkyl, $C_{2-10}$alkenyl, $C_{2-10}$alkynyl, $C_{3-12}$cycloalkyl, Het, aryl or $C_{1-10}$alkyl substituted with a substituent selected from the group consisting of Het, aryl, $C_{3-12}$cycloalkyl, amino and mono- or disubstituted amino wherein the substituents on the amino group are each individually selected from $C_{1-10}$alkyl, $C_{2-10}$alkenyl, $C_{3-12}$cycloalkyl, Het and aryl; or
$R^1$ and $R^2$ taken together with the nitrogen atom to which they are attached form a 5 to 12 membered saturated or partially saturated heterocycle with one or more heteroatoms each individually selected from nitrogen, oxygen or sulfur, and wherein said heterocycle may optionally be substituted with $C_{1-10}$alkyl, $C_{2-10}$alkenyl, $C_{2-10}$alkynyl, $C_{3-12}$cycloalkyl, $C_{1-6}$alkyloxycarbonyl, Het, aryl or $C_{1-10}$alkyl substituted with a substituent selected from the group consisting of Het, aryl, $C_{3-12}$cycloalkyl, amino and mono- or disubstituted amino wherein the substituents on the amino group are each individually selected from $C_{1-10}$alkyl, $C_{2-10}$alkenyl, $C_{3-12}$cycloalkyl, Het and aryl;
$R^3$ is carboxyl, halogen, nitro, $C_{1-10}$alkyl, $C_{3-12}$cycloalkyl, polyhalo$C_{1-10}$alkyl, cyano, amino, mono- or disubstituted amino, aminocarbonyl, mono- or disubstituted aminocarbonyl, $C_{1-10}$alkyloxy, $C_{1-10}$alkylthio, $C_{1-10}$alkylsulfonyl, pyrrolidinyl, piperidinyl, homopiperidinyl, morpholinyl, thiomorpholinyl or piperazinyl optionally substituted with $C_{1-10}$alkyl, wherein the substituents on any of the amino groups are each individually selected from $C_{1-10}$alkyl, $C_{2-10}$alkenyl, $C_{3-12}$cycloalkyl, Het and aryl;
aryl is phenyl optionally substituted with one or more substituents selected from the group consisting of $C_{1-10}$alkyl, polyhalo$C_{1-10}$alkyl, $C_{1-10}$alkyloxy, $C_{1-10}$alkylthio, $C_{1-10}$alkylsulfonyl, nitro, cyano, halo, $C_{3-7}$cycloalkyl, $C_{1-10}$alkylcarbonyl, carboxyl, $C_{1-10}$alkyloxycarbonyl, amino, mono- or disubstituted amino, aminocarbonyl, mono- or disubstituted aminocarbonyl, wherein the substituents on any of the amino groups are each individually selected from phenyl, $C_{1-10}$alkyl, $C_{2-10}$alkenyl, $C_{3-7}$cycloalkyl, pyrrolidinyl, piperidinyl, homopiperidinyl or piperazinyl optionally substituted with $C_{1-10}$alkyl;

Het is a 5 or 6 membered aromatic, saturated or partially saturated, monocyclic heterocycle with one or more heteroatoms each individually selected from nitrogen, oxygen or sulfur, and which heterocycle may optionally be substituted by one, or where possible, more than one substituent selected from the group consisting of $C_{1-10}$alkyl, polyhalo$C_{1-10}$alkyl, $C_{1-10}$alkyloxy, $C_{1-10}$alkylthio, $C_{1-10}$alkylsulfonyl, nitro, cyano, halo, $C_{3-7}$cycloalkyl, $C_{1-10}$alkylcarbonyl, carboxyl, $C_{1-10}$alkyloxycarbonyl, amino, mono- or disubstituted amino, aminocarbonyl, mono- or disubstituted aminocarbonyl, wherein the substituents on any of the amino groups are each individually selected from phenyl, $C_{1-10}$alkyl, $C_{2-10}$alkenyl, $C_{3-7}$cycloalkyl, pyrrolidinyl, piperidinyl, homopiperidinyl or piperazinyl optionally substituted with $C_{1-10}$alkyl.

d) $R^1$ and $R^2$ taken together with the nitrogen atom to which they are attached form a 5 to 12 membered saturated or partially saturated heterocycle which heterocycle may optionally be substituted with $C_{1-10}$alkyl, $C_{1-6}$alkyloxycarbonyl or $C_{1-10}$alkyl substituted with aryl;

e) L is $C_{1-2}$alkanediyl;

f) $R^3$ is halogen, nitro, $C_{1-10}$alkyl, $C_{3-12}$cycloalkyl, polyhalo$C_{1-10}$alkyl, cyano, $C_{1-10}$alkyloxy, $C_{1-10}$alkylthio, $C_{1-10}$alkylsulfonyl, piperidinyl, or morpholinyl;

g) aryl is phenyl optionally substituted with one or more substituents selected from the group consisting of $C_{1-10}$alkyloxy, halo, mono- or disubstituted amino, wherein the substituents on any of the amino groups are each individually selected from $C_{1-10}$alkyl;

h) Het is a 5 or 6 membered aromatic, saturated or partially saturated, monocyclic or bicyclic heterocycle with one or more heteroatoms each individually selected from nitrogen, oxygen or sulfur, and which heterocycle may optionally be substituted by $C_{1-10}$alkyl.

3. A compound as claimed in claim 1 having the formula:

4-[2-(4-Diethylaminomethyl-phenyl)-1,9b-dihydro-5-oxa-3,3a-diaza-cyclopenta[a]-naphthalene-4-carbonyl]-benzonitrile;

4-{2-[4-(Benzylamino-methyl)-phenyl]-1,9b-dihydro-5-oxa-3,3a-diaza-cyclopenta[a]-naphthalene-4-carbonyl}-benzonitrile;

4-[2-(4-{[(Pyridin-4-ylmethyl)-amino]-methyl}-phenyl)-1,9b-dihydro-5-oxa-3,3a-diaza-cyclopenta[a]naphthalene-4-carbonyl]-benzonitrile;

4-[2-(4-{[(4-Methoxy-benzyl)-methyl-amino]-methyl}-phenyl)-1,9b-dihydro-5-oxa-3,3a-diaza-cyclopenta[a]naphthalene-4-carbonyl]-benzonitrile;

(4-tert-Butyl-phenyl)-[2-(4-{[(4-methoxy-benzyl)-methyl-amino]-methyl}-phenyl)-1,9b-dihydro-5-oxa-3,3a-diaza-cyclopenta[a]naphthalen-4-yl]-methanone;

(4-tert-Butyl-phenyl)-[2-(4-{[(pyridin-4-ylmethyl)-amino]-methyl}-phenyl)-1,9b-dihydro-5-oxa-3,3a-diaza-cyclopenta[a]naphthalen-4-yl]-methanone;

(4-tert-Butyl-phenyl)-[2-(4-diethylaminomethyl-phenyl)-1,9b-dihydro-5-oxa-3,3a-diaza-cyclopenta[a]naphthalen-4-yl]-methanone;

4-{2-[4-(2-Diethylamino-ethyl)-phenyl]-1,9b-dihydro-5-oxa-3,3a-diaza-cyclopenta[a]-naphthalene-4-carbonyl}-benzonitrile;

4-(2-{4-[(Cyclopentyl-methyl-amino)-methyl]-phenyl}-1,9b-dihydro-5-oxa-3,3a-diaza-cyclopenta[a]naphthalene-4-carbonyl)-benzonitrile;

4-(2-{4-[4-(4-Methoxy-phenylamino)-butyl]-phenyl}-1,9b-dihydro-5-oxa-3,3a-diaza-cyclopenta[a]naphthalene-4-carbonyl)-benzonitrile;

(4-Methanesulfonyl-phenyl)-[2-(4-{[(pyridin-4-ylmethyl)-amino]-methyl}-phenyl)-1,9b-dihydro-5-oxa-3,3a-diaza-cyclopenta[a]naphthalen-4-yl]-methanone;

(4-Methanesulfonyl-phenyl)-[2-(4-{[(4-methoxy-benzyl)-methyl-amino]-methyl}-phenyl)-1,9b-dihydro-5-oxa-3,3a-diaza-cyclopenta[a]naphthalen-4-yl]-methanone;

[2-(4-Diethylaminomethyl-phenyl)-1,9b-dihydro-5-oxa-3,3a-diaza-cyclopenta[a]-naphthalen-4-yl]-(4-methanesulfonyl-phenyl)-methanone;

2. A compound as claimed in claim 1 wherein one or more of the following restrictions apply:

a) a is zero or 1;

b) $R^1$ is $C_{1-10}$alkyl, $C_{3-12}$cycloalkyl, Het, aryl or $C_{1-10}$alkyl substituted with a substituent selected from the group consisting of Het, aryl, $C_{3-12}$cycloalkyl and mono- or disubstituted amino wherein the substituents on the amino group are each individually selected from $C_{1-10}$alkyl;

c) $R^2$ is hydrogen, $C_{1-10}$alkyl, $C_{2-10}$alkenyl or $C_{1-10}$alkyl substituted with aryl;

or a N-oxide, stereoisomeric form or salt thereof.

4. A method of treatment comprising the systemic administration of an effective therapeutic amount of a compound as claimed in claim 1 to HIV-infected warm-blooded animals, in particular, HIV-infected humans.

5. A pharmaceutical preparation which as active constituents contain an effective dose of a compound as claimed in claim 1 in addition to customary pharmaceutically innocuous excipients and auxiliaries.

\* \* \* \* \*